United States Patent [19]

Takahashi et al.

[11] 4,106,329
[45] Aug. 15, 1978

[54] SOLID OR WATER QUANTITY MEASUREMENT APPARATUS USING MICROWAVES

[75] Inventors: Yoshiyuki Takahashi, Aikawamachi; Akihiko Nagai, Ebina; Shigenobu Kawawa, Machida; Hidetaka Kubozono; Mitsuo Tanaka, both of Atsugi, all of Japan

[73] Assignee: Anritsudenki Kabushikigaisha, Tokyo, Japan

[21] Appl. No.: 790,992

[22] Filed: Apr. 26, 1977

[30] Foreign Application Priority Data

Apr. 26, 1976 [JP] Japan ............................... 51-46514

[51] Int. Cl.² ............................................. G01N 5/04
[52] U.S. Cl. ........................................ 73/15 B; 73/76
[58] Field of Search .......... 73/76, 15.4, 15 B, 61.1 R; 219/10.55 R, 10.55 M

[56] References Cited

U.S. PATENT DOCUMENTS

| | | | |
|---|---|---|---|
| 3,813,918 | 6/1974 | Moe | 73/76 X |
| 3,909,598 | 9/1975 | Collins et al. | 219/10.55 X |
| 3,916,670 | 11/1975 | Davis et al. | 73/76 X |

Primary Examiner—Charles A. Ruehl
Attorney, Agent, or Firm—Staas & Halsey

[57] ABSTRACT

An apparatus for measuring water in cow's milk. Sample milk is heated and dryed by microwaves in an oven made of a microwave waveguide. Weights of the sample before and after the drying of the sample are measured by an automatic balance. Weight signals obtained from the balance are memorized in a memory circuit to calculate the solid material ratio or water ratio of the sample milk. A water dummy is employed for stabilizing oven temperature. Support means for one or more additional sample plates may be arranged in the waveguide for preliminary drying of one or more filter paper in the additional sample plate to shorten the subsequent heating time of the sample milk.

13 Claims, 11 Drawing Figures

SOLID OR WATER QUANTITY MEASUREMENT APPARATUS USING MICROWAVES

BACKGROUND OF THE INVENTION

The present invention relates to a solid or water quantity measurement apparatus using microwaves for the measurement of the solid quantity and/or water quantity of liquid or viscous material such as cow's milk and soy which include solid material and water.

Cow's milk comprises some quantity of fat, protein, milk sugar, ash and water, the quantity of which is not always constant. The content changes according to breed of cows, feed, season, condition of cows health and others. Thus, it is best in business to decide the price of cow's milk in accordance with the contents of the milk. However, measurement of the content requires a relatively long time. Therefore, the determination of the milk price depends on the measurement of fat at the present time. The fat measurement requires relatively short time. (Official methods for measurement, such as the Gerber method and the Babcock method, require about 2 hours / 12 samples, and its photo-turbiditymeter method, which uses a milk checker or a milk tester, requires about 20 seconds / 1 sample.)

There was in the past a relationship between the quantity of the fat of cow's milk and the quantity of other materials in the milk, and the latter was proportional to the former. However, there is no relationship between the fat quantity and other materials in cow's milk today because cows which produced milk of small quantity of fat have been reduced and those producing milk of large quantity of fat have been increased. As a result, cows which produce milk of large quantity of fat are today being normally fed at farms. Those cows sometime produce milk of small quantity of solid materials (milk sugar, protein and ash) in spite of large quantity of fat, and this is a serious problem.

Recently, therefore, it has been suggested that the transaction of cow's milk should be determined on the basis of measurement of total solid quantity, including fat and other all solid materials, although the transaction on the basis of respective quantity of each material in the milk is best. However, the official measurement method of total solid quantity of the milk is its heat drying method which requires 7 hours to 8 hours for the measurement. Thus more than ten or more samples can not be measured by the heat drying method in a day.

There are other methods for measurement, for example, specific gravity meters, lactometer methods, plastic bijou methods, Mojonnier methods, infrared rays total solid measurement methods, microwave heating methods and microwave heating water meter methods.

The specific gravity meter method includes the measurement of specific gravity of cow's milk and estimation of total solid quantity rate of the milk. However this method is not accurate enough to utilige in the transaction of cow's milk. The total solid rate in the milk can be shown and temperature compensation introduced into the measured value of the total solid rate by the lactometer method. However this method gives errors as much as ± 0.12 % TMS (TMS: Total milk Solid.). The plastic bijou method utilizes 10 bijous of 10 colors made of poly-methyl-styrene, each of the bijous corresponding to a the specific gravity difference of 0.001. Specific gravity of cow's milk can be determined by numbers and colors of bijous above, and under the surface of the milk. Thus, the plastic bijou method is practiced easily but is inaccurate. The Mojonnier tester method includes the preliminary heating of cow's milk at 180° C on a plate, main heating at 100° C ± 1° C in a vacuum furnace after preliminary heating, and cooling after the main heating and measurement of a solid remaining on the plate. This method can be carried out speedily however, it is costly and gives measurement deviation from that of the official method. Thus the Mojonnier tester method has been rarely practised. The infrared rays total solid measurement method includes impregnation of cow's milk of 0.97 ml which corresponds to 1g weight into a filter paper, preliminary heating of the filter paper on a aluminum plate and heating (75° C) in an infrared ray furnace to evaporate water. The infrared ray furnace is not sealed hermetically, so that the dryed sample in the furnace absorbes water in the air. The time interval between drying the sample and measurement of the quantity of the dryed sample is not constant because of the manual transportation of the sample from the drying stage to the measurement stage. This causes a difference in the absorbed water among the dryed samples at the measurement stage and the absorbed water effects its measurement accuracy. The calculation of %TMS requires 3 members in this method with manual calculation. More than 300 samples can not be measured in a day.

The microwave heating method employs a so-called electron range (microwave oven) to dry the cow's milk. The microwave oscillator is separated from the microwave oven because of the higher power of the drying sample of milk. Since the microwave drying method merely utilizes microwave heating instead of the air flow heating of the official method, it requires the same steps for the solid measurement of the official method. As a result, it requires a relatively long time for measurement. Also, a turn table is required in the oven because the electric field destribution in the range is not uniform. This makes it impossible to achieve a balance in the oven. Thus, direct reading of the balance in the oven is impossible. In addition, its temperature in the oven rises in accordance with the repeating of the measurements. Moreover, the wall surface of the oven is relatively low in temperature, which causes condensation of evaporated water. Thus, condensed water falls on the sample. The microwave drying method is thus a complex process.

The microwave heating water meter method employs the same theory as the microwave heating method as described above. However, a balance is achieved with the microwave oven, and thus the sample is not required to be carryed out of the oven to measure its weight, and direct reading of the weight of the sample is possible by the balance. Nevertheless, the temperature in the oven rises as its measurements are repeated. This has an effect on the accuracy of the measurement. Also, electric field distribution in the oven is insecure and not uniform. Therefore a stirrer is required. A large quantity of the sample milk is required, and condensed water appears on the surface of the oven.

SUMMARY OF THE INVENTION

It is therefore an object of the present invention to provide a solid or water quantity measurement apparatus using a microwave, which can easily and quickly measure solid quantity in a liquid or viscous material, e.g. cow's milk.

A further object of the present invention is to eliminate the problems or defects of the prior arts described hereinbefore.

Other objects of the invention will be apparent from the detailed description of the invention described hereinafter referring to the attached drawings.

According to the present invention, a waveguide is employed so as to utilize its inter space as an oven. A microwave oscillator is assembled with the wageguide at its one end. A dummy is connected to the other end of the waveguide. The electric field in the waveguide as a oven is a stabilized mode, so that the electric field in the oven of the present invention is uniform and secure. This makes unnecessary the use of the stirrer. A dummy can absorb microwaves, and thus microwave reflection in the oven is reduces. Microwave irradiation onto the antenna of the microwave oscillator is reduced by the dummy. Therefore the antenna has a long life.

According to the present invention, a balance is achieved with the waveguide. The weight detection plate of the balance is arranged in the waveguide. The sample plate for the main heating of the sample is on the weight detection plate and removable from it.

Further, according to the present invention evaporated water discharge means is assembled with the waveguide, which prevents the occurrence of condensed water on the inner surface of the oven.

Generally speaking, the dielectric power absorption P with respect to a microwave can be shown as follows:

$$P = 0.556 f E^2 \epsilon r \tan\delta \times 10^{-10} \, (W/m^3)$$

wherein
 $f$: frequency (Hz),
 $E$: electric field strength (V/m),
 $\epsilon r$: specific inductive capacity, and
 $\tan\delta$: dielectric loss tangent.

Thus, the power absorption of a dielectric is proportional to the product of the frequency $f$, the square of electric field strength E, the specific inductive capacity $\epsilon r$ and the dielectric loss tangent $\tan\delta$. Usually, since the electric field strength E and frequency f are constant, the dielectric power absorption P depends on the dielectric loss $\epsilon r \cdot \tan \delta$.

Since the water molecule has a strong permanent dipole moment, and shows strong dielectric attenuation caused by rotational polarization at microwave range (field), the dielectric loss $\epsilon r \cdot \tan \delta$ of water is a large value. For example, the dielectric loss of water at 3 GHz frequency is about as much as 12 (at 25° C). On the other hand, other materials show very little dielectric loss (for example, quartz glass shows 0.0005). Thus, water absorbs large amounts of microwave power and becomes dry very quickly, as compared with another materials.

Figure 1:
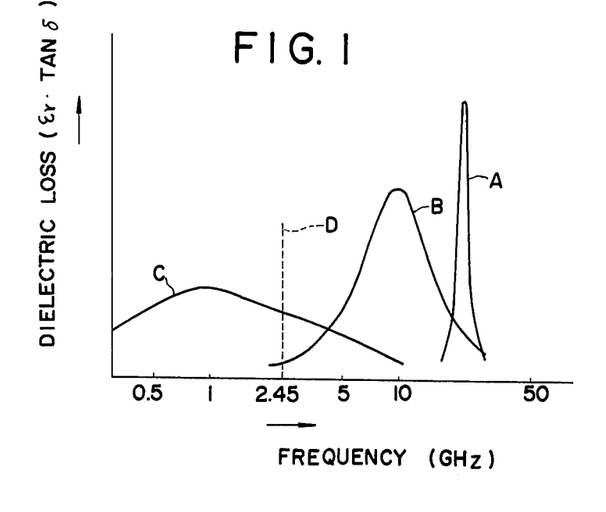
FIG. 1 shows the microwave dielectric loss of water, in which curve A denotes the dielectric loss of water vapor, curve B denotes the dielectric loss of liquid water, and curve C denotes the dielectric loss of bound water.

However, since rotational polarization depends on the viscosity of the microwave propagation medium, the rotational polarization changes according to viscocity parameters e.g. condition of water (vapor, liquid, solid or bound water) and temperature. Thus the dielectric loss, i.e. power absorption of water, depends on the condition of the water and its temperature. FIG. 1 shows the dielectric loss of water in contrast to its microwave frequency. In FIG. 1, the curve A shows the dielectric loss of water vapor, the curve B shows that of liquid water, and the curve C shows that of bound water. The broken line D shows 2.45 GHz of the cross axis which represents the microwave oscillator frequency. As can be seen in FIG. 1, there is much dielectric loss of microwave of 2.45 GHz in liquid water (curve B). This means that in the case when a cow's milk is impregnated in a filter paper and dryed by microwaves, bound water within the filter paper and bound water within the milk contribute to the main dielectric loss, i.e. absorption of microwave energy to dry up. This absorbed energy transfers into liquid water to heat up and vaporize it. As seen in FIG. 1, liquid water (curve B) has little dielectric loss at 2.45 GHz, and therefore liquid water without bound water (curve C) is scarcely heated up to vapourize at 2.45 GHz.

Figure 2:
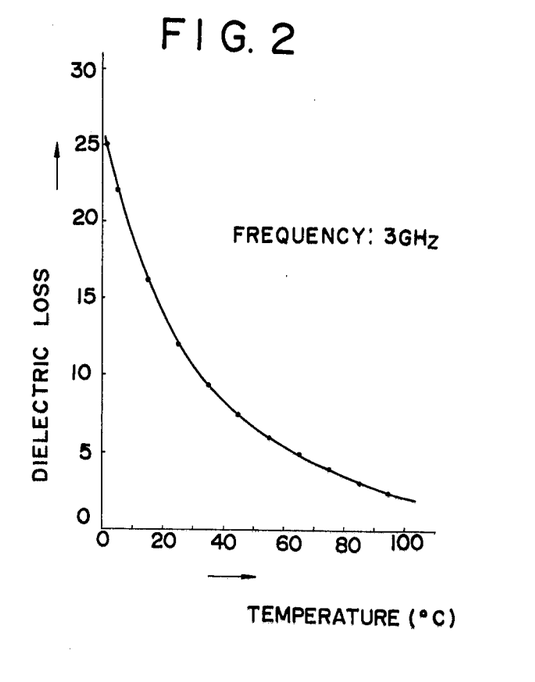
FIG. 2 is a graph showing the dielectric loss of water with respect to the water temperature.

FIG. 2 shows the dielectric loss of water in contrast to temperature. As seen in FIG. 2, the dielectric loss of water greatly changes in relationship with the water temperature.

Therefore, in a preferred embodiment of the present invention the dummy at one end of the waveguide comprises a water receiver (water dummy) for stabilizing the temperature in the waveguide. One or more support members for the preliminary heating of the filter papers are preferably arranged in the waveguide. The preliminary heating of the filter paper on the support member shortens the subsequent main heating of the sample on the weight detection plate of the balance and gives an accurate measurement result. Thus the preliminary heating of a filter paper is practiced in the waveguide at the same time with the main heating of a sample. Further, mechanical movement of the balance is preferably converted into a electric signal which, in turn, is memorized and calculated to display the solid ratio otherwise water ratio of the sample. This makes easy to obtain the measurement result with direct reading.

DESCRIPTION OF THE PREFERRED EMBODIMENT

Figure 3:
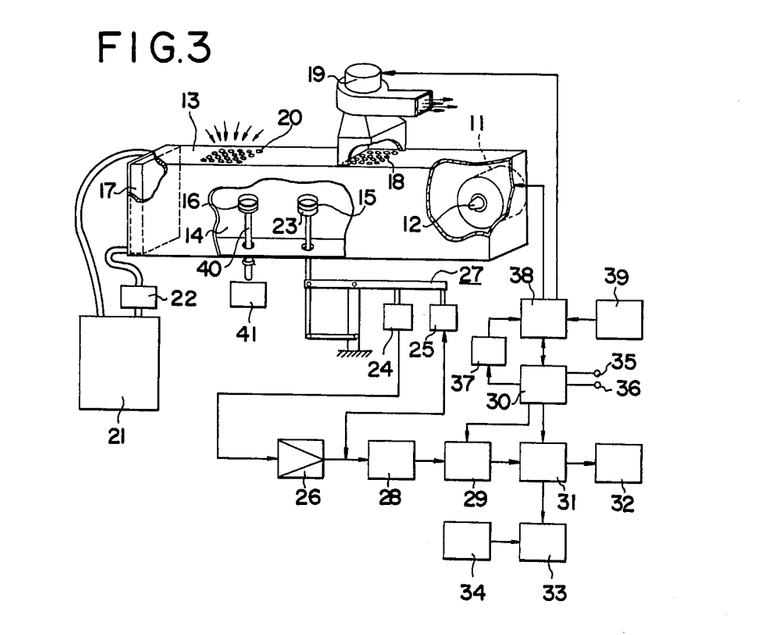
FIG. 3 is a diagram of the preferred embodiment of the present invention, in which the microwave heating apparatus is shown in perspective and the other components such as electric circuits and electronic devices are shown with block diagram.

Referring to FIG. 3, a microwave of $TE_{10}$ mode emitted from an antenna 12 of a magnetron 11 is absorbed in water in the main heating sample plate 15 and additional sample plate 16, the plates 15 and 16 being arranged in interspace or oven 14 enclosed by a waveguide 13. The water in the plates 15 and 16 is heated by the microwave absorption. Remainder microwave not absorbed by the water in the plates 15 and 16 is absorbed by water in a water dummy 17. Evaporated water from the main heating sample plate 15 and the additional sample plate 16 is discharged out of the waveguide 13 through a plurality of exhaust openings 18 with a fan 19. Air is supplyed into the waveguide 13 through a plurality of air supply openings 20 with the fan 19.

As described hereinbefore in relationship to FIG. 2, the dielectric loss $\epsilon r \cdot \tan\delta$ of water greatly changes in accordance with the temperature of water, therefore, if the temperature of water in the water dummy 17 should not be constant, the time interval for drying the sample in the plate 15 will vary sometimes. Thus, it is preferable to circulate water in the water dummy 17 through a water pyrostat tank 21 by a pump 22.

The main heating sample plate 15 is placed on a weight detection plate 23 in the waveguide 13. The weight detection plate 23 is connected with one end of an arm member, the other end of which is out of the waveguide 13 and connected with an automatic balance 27. The automatic balance 27 includes balance check 24, force coil 25 and amplifier 26. The automatic balance 27 generates an analog electric signal which represents the total weight of the sample plate 15 and the sample on the plate 15. The analog electric signal from the amplifier 26 of the balance 27 is converted into a digital signal through an A/D converter 28, and then memorized in a memory circuit 29. The memorized digital signal in the memory circuit 29 will be read out by a signal from a command circuit 30 and supplied into a calculator 31. The calculator 31 supplys an output data signal to a display 32 and a printer 33. The printer 33 prints out the data from the calculator 31 including the, date, group indication number and farmer indication number. A date indicator 34 sets the date to be printed out.

By pressing down tare deduction button 35, a tare weight of the sample plate and a filter paper on the plate 15 is memorized in the memory circuit 29. By pressing down measurement button 36, the total weight including sample milk on the main heating plate 15 is memorized in the memory circuit 29. The pressing down of the measurement button 36 actuates a timer 38 after a predetermined delay time through a delay circuit 37. Power source 39 supplys regulated electric power to the magnetron 11 and so on. There is a plate support 40, an end of which is in the waveguide 13 to support additional sample plate 16 for preliminary heating of a filter paper and the other end of which is out of the waveguide and connected with a pressure detector switch 41.

Figure 4:
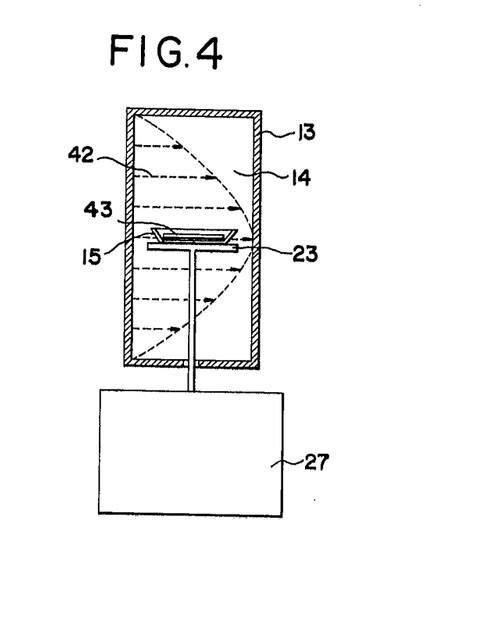
FIG. 4 is an enlarged cross sectional view of the waveguide 13 shown in FIG. 3.

FIG. 4 is a cross sectional view of the waveguide 13 vertical to the transmitting direction of the microwave. The electric field distribution 42 in the oven 14 is a stabilized $TE_{10}$ mode as shown with a broken line curve. A filter paper 43 made of fibers such as glass fibers is put on the sample plate 15. The sample is impregnated in the filter 43. The sample plate 15 on the weight detection plate 23 is arranged at the maximum electric field, i.e. the center of the waveguide 13. The stabilized $TE_{10}$ mode stabilizes the heating condition of the sample and the sample heating time. Arrangement of the filter paper 43 at the center of the waveguide 13 shortens the sample heating time.

The operation of the apparatus shown in FIG. 3 will now be described. The main heating sample plate 15 on the weight detection plate 23 is removed after the preceeding sample in the sample plate 15 is finished. A filter paper in the additional sample plate 16 on the plate support 40 is heated by the preceeding heating of the sample on the weight detector plate 23. The additional sample plate 16 having the heated filter is put on the weight detector plate 23. A sample plate having a new filter paper is put on the plate support 40. Then the tare deduction button 35 is pressed down by an operator, by which the total weight of the sample plate on the weight detection plate 23 and the filter paper in the sample plate is memorized in the memory circuit 29. Then a sample (for example 1g of cow's milk) is put on or impregnated in the filter paper on the weight detection plate 23.

The use of the filter paper prevents sputtering of the milk and occurrence of fat film on the surface of heated milk, the fat film preventing efficient drying of the milk. Bound water which absorbs much microwave energy is increased by the use of the filter paper. This shortens the heating time of the sample.

Then the measurement button 36 is pressed down, by which the total weight $W_1$ of the tare and sample is memorized in the memory circuit 29. A signal from the button 36 after a predetermined delay time in which the weight $W_1$ is memorized in the memory circuit 29 actuates the timer 38. The actuation of the timer 38 closes a switch in the timer 38, by which the magnetron 11 is energized from the power source 11. The magnetron 11 then generates and emits a microwave into the oven 14. The timer 38 at the same time drives the fan 19.

After a predetermined time limit which is appropriate for drying the sample on the weight detection plate 23, the timer 38 interrupts the elctric power from the power souce 39 to magnetron 11 and fan 19. Thus the microwave from the magnetron 11 disappears. At the same time the timer 38 supplys a time over signal to the command circuit 30. Then the command circuit 30 supplys memory command signal to the memory circuit 29. Thus total weight $W_2$ of the tare and dryed up sample is memorized in the memory circuit 29. The calculator 31 is constructed so as to calculate the water ratio $[(W_1 - W_2)/(W_1 - W_o)] \times 100$ (% $H_2O$) and/or the solid ratio $[(W_1 - W_o)/(W_1 - W_o)] \times 100$ (% TMS) from the tare weight $W_o$ (the filter paper is preliminary dryed up), the total weight $W_1$ of the tare and the sample (the sample is not dryed up) and the total weight $W_2$ of the tare and the dryed sample, all of which are memorized in the memory circuit 29. The so calculated water ratio and/or solid ratio is displayed on the display 32 and printed out by the printer 33. The pressure detector switch 41 can be used for a additional sample plate 16 indication. For example, a warning lamp may be actuated by the switch 41 when the additional plate 16 is absent.

Figure 5A:
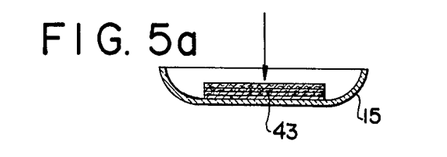
FIG. 5a is an enlarged cross sectional view of a sample plate to be used in the present invention.

FIG. 5a shows a cross section of a preferred sample plate which can be employed as an additional plate for the preliminary heating and main heating sample plate. The sample plate 15 shown in FIG. 5a has a concaved brim and flat base for arranging the filter paper 43 on it.

Figure 5B:
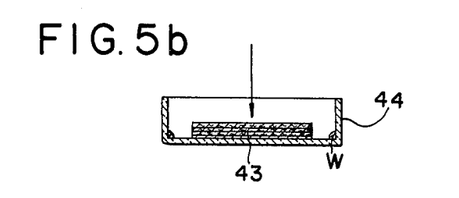
FIG. 5b is an enlarged cross sectional view of a sample plate which is unsuitable for microwave heating.

FIG. 5b is a cross section of another sample plate 44 which is not suitable for microwave heating of a liquid sample. Evaporated water from the glass filter 43 in the sample plate 44 condenses at the surface of the sample plate 44. The condensed water W remains in the sample plate 44. The condensed water W is scarcely evaporated from the sample plate 44 because liquid water absorbs little microwave energy at 2.450 MHz as shown in FIG. 1 (curve B).

On the other hand, the evaporated water from the filter paper 43 in the sample plate 15 shown in FIG. 5a easily escapes from the sample plate 15 because of its concave brim, which results in no condensation of water vapor. And if condensation should occur, the condensed water comes into the filter paper along the concave brim. Then the water is impregnated in the filter paper. This impregnated bound water absorbs much microwave energy as shown in FIG. 1 (curve C) and is dryed faster. The sample plate 15 shown in FIG. 5a is also easy to handle for cleaning. The condensed water W in the sample plate 44 shown in FIG. 5b will come into the filter paper 43 when the filter paper 43 is large enough to attach with the vertical wall of the plate 44. However, evaporated water from the filter plate escape mainly from circular edge of the paper 43 since the fibers in the paper 43 are parallel with the flat base of the sample plate 44. Therefore, a filter paper which is large enough to attach with the vertical wall of the plate 44 will interrupt the escape of water vapor from the circular edge of the filter paper. This results in the drying up of the filter paper and the sample takes a long time. The sample plate 44 is relatively difficult to handle for cleaning. Therefore, the sample plate 15 having concaved brim is preferred for microwave drying. The sample plate 15 is preferably made of a material such as a glass which shows low reflection and absorption of microwaves.

Figure 6:
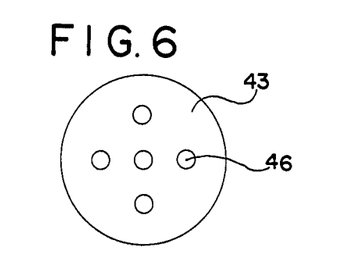
FIG. 6 is an enlarged plane view of a preferred filter paper for the present invention.

FIG. 6 shows a plan view of a filter paper 43 which is preferred for fast drying. The filter paper has a plurality of openings 46, which allows the escape of water vapor in the filter paper 43 at the circular edge of the filter paper. Thus, the openings 46 contribute to the uniform and speedy drying of the filter and the sample. The number and diameter of the openings 46 may be selected in accordance with the kind and quantity of the sample.

Figure 7:
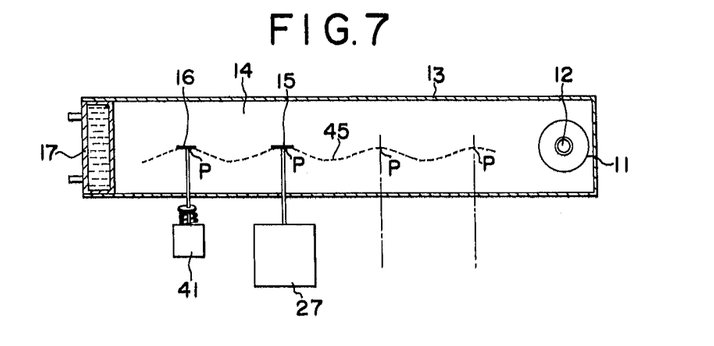
FIG. 7 shows an axial cross sectional view of a waveguide of another embodiment of the invention.

FIG. 7 shows a longitudinal cross section of the waveguide of another embodiment, and especially suitable positions of the main heating sample plate 15 and the additional sample plate for preliminary heating. The microwaves emitted into the oven 14 from the antenna 12 of the magnetron 11 are at first absorbed in the filter paper and the sample in the sample plate 15, then absorbed in the filter in the additional sample plate 16, and finally absorbed in the water in the water dummy 17. All of the microwaves emitted from the antenna can not be absorbed throughly, a part of them being reflected at the water dummy 17. The reflected microwaves causes a standing wave with the emitted microwave. Since the electric field of the standing wave is maximum at its wave crests, it is preferable to place the sample plate 15 and the additional sample plate 16 at the wave crests of the standing wave to dry the filter papers and the sample faster. The sample plate 15 and additional sample plate 16 in the preceeding embodiment shown in FIG. 3 may be preferably placed at the wave crests. Moreover, more than two sample plates are can be placed at the wave crests in the waveguide 13, in which case the waveguide may be preferable to be longitudinally elongated.

Figure 8:
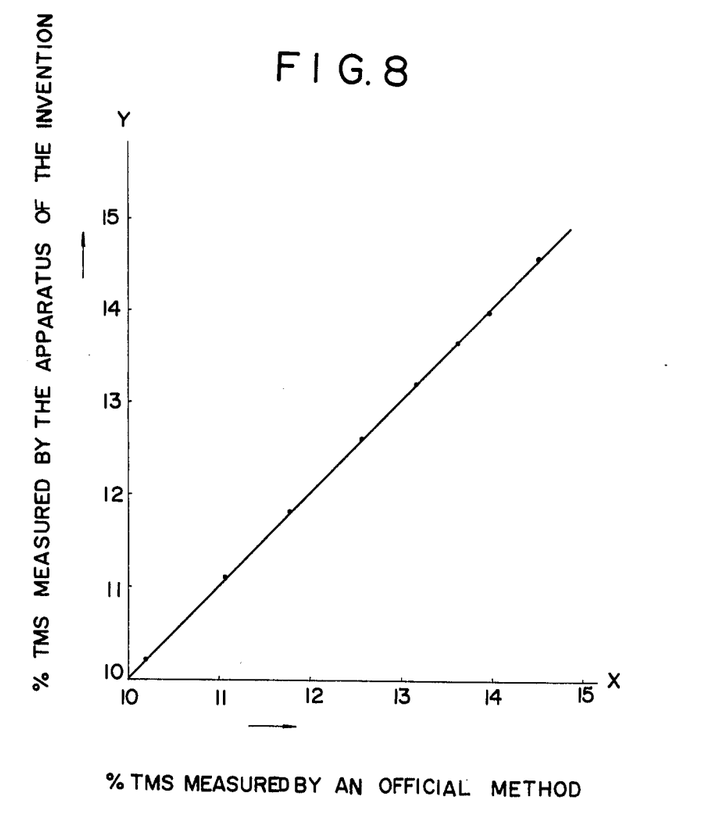
FIG. 8 is the graph showing a relationship between the measurement data using the present invention and that of the official method.

FIG. 8 shows the relationship between the % TMS measured by a preferred embodiment of the present invention and that of an official method. The dots in the graph of FIG. 8 show samples of different % TMS. The cross axis represents measured % TMS values X of an official method and the vertical axis represents measured % TMS values Y by a preferred embodiment of the present invention. The line in the graph shown in FIG. 8 is represented by a regression formula $Y = 1.0115X - 0.127$, the correlation constant $Y = 1.0000$ and standard deviation from the regression 0.01474 (% TMS), all of which are superior.

Figure 9:
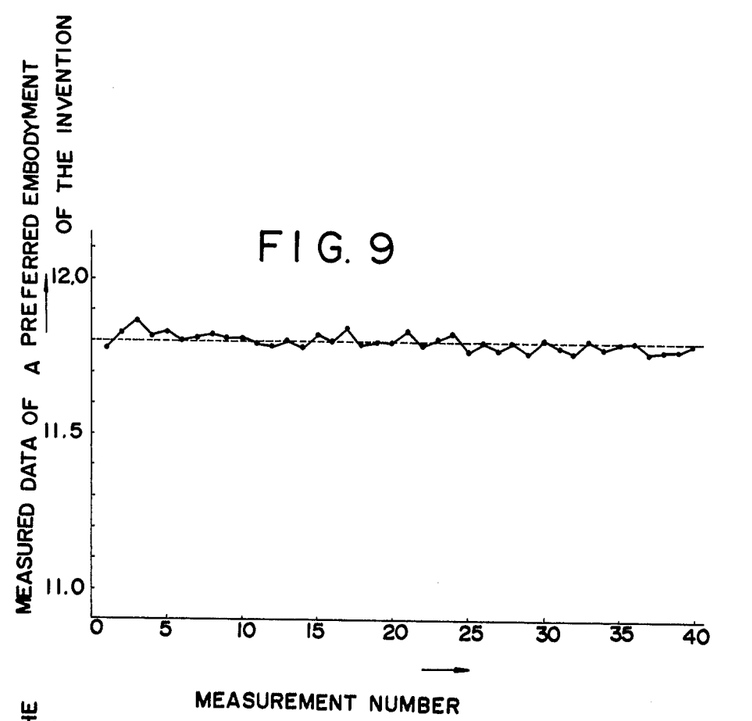
FIG. 9 is a graph showing a number of measured data of the present invention, the sample being the same at each measurement.

FIG. 9 shows sample data distribution with respect to the same sample. A group of 40 samples were prepared from the same cow's milk of constant solid material ratio and measured by an apparatus of the present invention. The measured data of 40 samples were plotted on the graph shown in FIG. 9. The standard deviation of the data shown in FIG. 9 is 0.022 (% TMS) and range (maximum value − minimum value) is 0.1 (% TMS), those are small.

Figure 10:
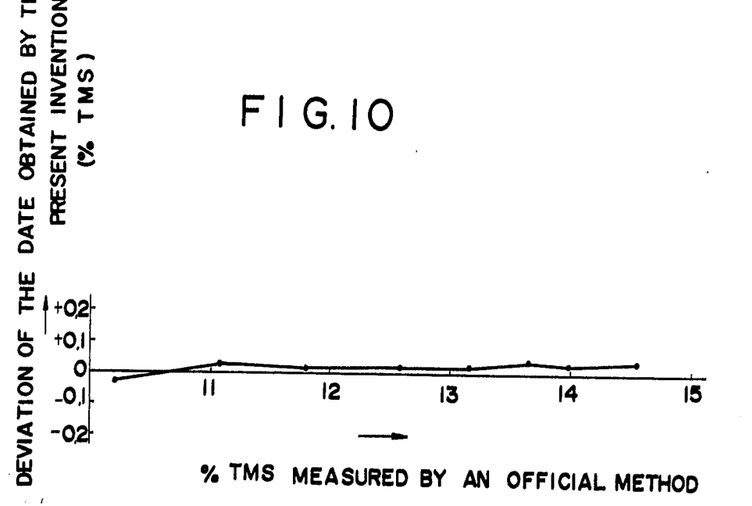
FIG. 10 is a graph showing deviations of the measured data of the present invention from that of the official method.

FIG. 10 shows deviations of the data obtained by the apparatus of the present invention from that measured by an official method. The deviations shown in FIG. 10 are within ±0.05 (% TMS), which is a very small value.

As will be apparent from the foregoing disclosure, the apparatus of the present invention is utilized not only for cow's milk but also for other materials having water or vaporizable substances. The apparatus can, because of its operation, measure not only the solid material ratio but also the water ratio of samples.

The foregoing disclosure is representative of the preferred embodiments of the invention. It should be understood that various modifications and alternatives may be adopted and utilized by those skilled in the art without departing from the spirit and scope of the invention which is in accordance with the claims appended hereto. For example the water dummy 17 may be exchanged with another dummy.

We claim:

1. A solid or water quantity measurement apparatus using microwaves, comprising:
   a waveguide forming an oven with an inner space and two ends, at one end of which a microwave oscillator is assembled and at the other end of which a dummy is assembled;
   a balance having a weight detection plate in said waveguide and assembled with said waveguide;
   means for discharging evaporated water in said waveguide away from said waveguide; and
   a sample plate attachable on and detachable from said weight detection plate in said waveguide.

2. A solid or water quantity measurement apparatus using microwaves as defined in claim 1, wherein said dummy is a water dummy which receives constant temperature water from a pyrostat tank.

3. A solid or water quantity measurement apparatus using microwaves as defined in claim 1, wherein said balance is an automatic balance and further comprises a memory circuit for memorizing weight signals from said balance, a calculator which calculates the solid material ratio or water ratio from the memorized signals in said memory circuit, and a display means.

4. A solid or water quantity measurement apparatus using microwaves as defined in claim 1, wherein said means for discharging evaporated water in said waveguide away from said waveguide comprises one or more openings for discharging evaporated water, one or more openings for supplying air into the waveguide, and a fan.

5. A solid or water quantity measurement apparatus using microwaves as defined in claim 1, wherein said sample plate has a concave brim.

6. A solid or water quantity measurement apparatus using microwaves as defined in claim 1, further comprising a filter paper on said sample plate, said filter paper having one or more openings.

7. A solid or water quantity measurement apparatus using microwaves, comprising:
- a waveguide forming an oven with an inner space and two ends, at one end of which a microwave oscillator is assembled and at the other end of which a dummy is assembled;
- a balance having a weight detection plate in said waveguide and assembled with said waveguide;
- means for discharging evaporated water in said waveguide away from said waveguide;
- support means in said waveguide for one or more additional sample plates; and
- a plurality of sample plates attachable on and detachable from said weight detection plate and said support means in said waveguide.

8. A solid or water quantity measurement apparatus using microwaves as defined in claim 7, wherein said dummy is a water dummy which receives constant temperature water from a pyrostat tank.

9. A solid or water quantity measurement apparatus using microwaves as defined in claim 7, wherein said balance is an automatic balance and further comprises a memory circuit for memorizing weight signals from said balance, a calculator which calculates the solid material ratio or water ratio from the memorized signals in said memory circuit, and a display means.

10. A solid or water quantity measurement apparatus using microwaves as defined in claim 7, wherein said means for discharging evaporated water in said waveguide away from said waveguide comprises one or more openings for discharging evaporated water, one or more openings for supplying air into the waveguide, and a fan.

11. A solid or water quantity measurement apparatus using microwaves as defined in claim 7, wherein said sample plates have concaved brims.

12. A solid or water quantity measurement apparatus using microwaves as defined in claim 7, further comprising filter papers on said sample plates, each of said filter papers having one or more openings.

13. A solid or water quantity measurement apparatus using microwaves as defined in claim 7, wherein said support means has sensor means which detect said sample plate on said support means.

* * * * *

UNITED STATES PATENT OFFICE
CERTIFICATE OF CORRECTION

Patent No. 4,106,329                    Dated August 15, 1978

Inventor(s) Yoshiyuki Takahashi et al.

It is certified that error appears in the above-identified patent and that said Letters Patent are hereby corrected as shown below:

Col. 1, line 65, delete "the"

Col. 2, line 7, after "speedily" insert --;--

Col. 2, line 53, change "carryed" to --carried--

Col. 3, line 9, change "wageguide" to --waveguide--

Col. 3. line 16, change "reduces" to --reduced--

Col. 3, line 41, change "f" to --$f$--

Col. 3, line 54, change "materials" to --material--

Col. 4, lines 10 & 11, change "vapourize" to --vaporize--

Col. 4, line 30, change "a" to --an--

Col. 5, line 41, change "supplys" to --supplies--

Col. 5, line 43, after "the" (2nd occasion) delete --,--

Col. 5, line 54, change "supplys" to --supplies--

UNITED STATES PATENT OFFICE
CERTIFICATE OF CORRECTION

Patent No. 4,106,329  Dated August 15, 1978

Inventor(s) Yoshiyuki Takahashi et al.

It is certified that error appears in the above-identified patent and that said Letters Patent are hereby corrected as shown below:

Col. 6, line 40, change "elctric" to --electric--

Col. 6, line 43, change "supplys" to --supplies--

Col. 6, line 44, change "supplys" to --supplies--

Col. 7, line 55, change "throughly" to --thoroughly--

Col. 7, line 65, delete "are"

Signed and Sealed this

Twenty-seventh Day of March 1979

[SEAL]

Attest:

RUTH C. MASON  
Attesting Officer

DONALD W. BANNER  
Commissioner of Patents and Trademarks